(12) United States Patent
Darr et al.

(10) Patent No.: US 8,979,803 B2
(45) Date of Patent: Mar. 17, 2015

(54) STYLET FOR BILUMENAL FLEXIBLE MEDICAL DEVICE

(76) Inventors: Allan J. Darr, Centre Hall, PA (US); Einar Petersen, Maaloev (DK)

(*) Notice: Subject to any disclaimer, the term of this patent is extended or adjusted under 35 U.S.C. 154(b) by 0 days.

(21) Appl. No.: 13/412,468

(22) Filed: Mar. 5, 2012

(65) Prior Publication Data

US 2013/0035609 A1    Feb. 7, 2013

Related U.S. Application Data

(63) Continuation-in-part of application No. 12/660,058, filed on Feb. 19, 2010, now abandoned, which is a continuation-in-part of application No. 11/784,142, filed on Apr. 5, 2007, now Pat. No. 7,704,234.

(51) Int. Cl.
*A61M 5/178* (2006.01)
*A61M 25/00* (2006.01)
*A61B 10/02* (2006.01)
*A61M 25/01* (2006.01)
*A61M 25/06* (2006.01)

(52) U.S. Cl.
CPC ........ *A61M 25/0054* (2013.01); *A61B 10/0275* (2013.01); *A61M 25/0136* (2013.01); *A61M 25/0138* (2013.01); *A61M 25/065* (2013.01)
USPC ...................................................... 604/164.1

(58) Field of Classification Search
USPC ............. 604/164.1, 164.11, 164.13; 600/564, 600/565, 566, 567
See application file for complete search history.

(56) References Cited

U.S. PATENT DOCUMENTS

| | | | | |
|---|---|---|---|---|
| 5,273,051 A | * | 12/1993 | Wilk | 600/564 |
| 5,336,191 A | * | 8/1994 | Davis et al. | 604/165.01 |
| 5,601,588 A | * | 2/1997 | Tonomura et al. | 606/185 |
| 6,015,391 A | * | 1/2000 | Rishton et al. | 600/567 |
| 6,261,243 B1 | * | 7/2001 | Burney et al. | 600/564 |
| 6,371,943 B1 | * | 4/2002 | Racz et al. | 604/274 |
| 6,419,641 B1 | * | 7/2002 | Mark et al. | 600/564 |
| 7,022,106 B2 | * | 4/2006 | Jorgensen | 604/103.09 |
| 7,048,694 B2 | * | 5/2006 | Mark et al. | 600/564 |
| 7,101,361 B2 | * | 9/2006 | Gardeski | 604/523 |
| 7,128,956 B2 | * | 10/2006 | Wang et al. | 428/36.9 |
| 7,147,607 B2 | * | 12/2006 | Wang | 600/566 |
| 7,204,812 B2 | * | 4/2007 | Wang | 600/566 |
| 8,224,457 B2 | * | 7/2012 | Strandberg et al. | 607/116 |
| 2004/0068308 A1 | * | 4/2004 | Gellman et al. | 607/103 |
| 2004/0133124 A1 | * | 7/2004 | Bates et al. | 600/564 |
| 2005/0159676 A1 | * | 7/2005 | Taylor et al. | 600/567 |

* cited by examiner

*Primary Examiner* — Aarti B Berdichevsky
(74) *Attorney, Agent, or Firm* — Oliff PLC

(57) ABSTRACT

Utilizing the technology and methods disclosed, the characteristics of flexibility and rigidity for intralumenal devices, including coaxial two piece devices such as stylet and needle sets, can be adapted by a physician or device manufacturer according to the type of procedure, the patient size and unique anatomical challenges of a given procedure. Rigidity and flexibility are actively controlled by the operator at predefined portions of a device through rotating the stylet within the cannula to bring about alignments of customized notches to impart target flexibility or rigidity profiles at specific spots on the device. The device operator is able to alter the relationship and orientation of specific notched and non-notched segments of either or both the stylet and cannula that are strategically located at said critical points along the length of the device.

16 Claims, 8 Drawing Sheets

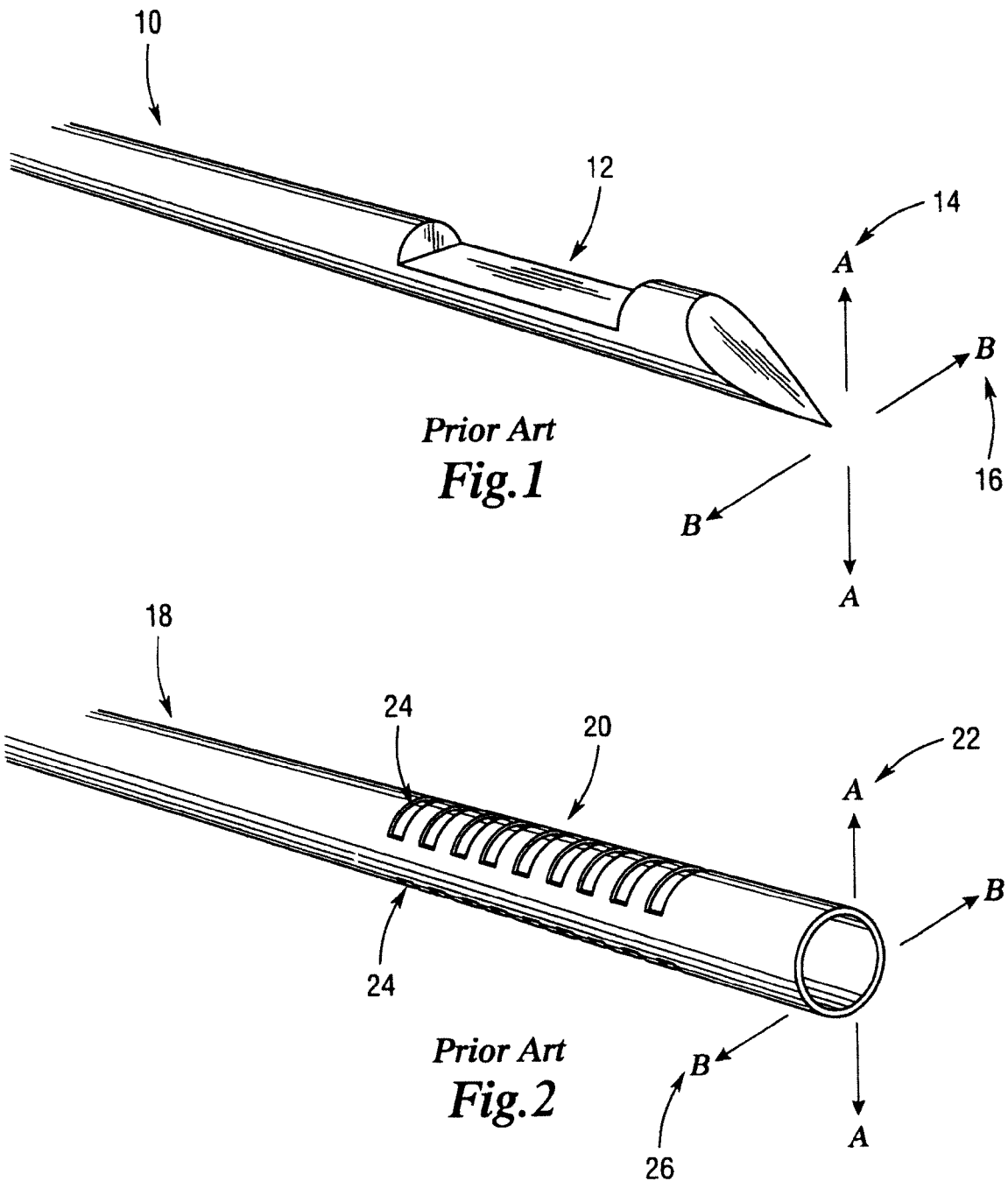

STYLET FOR BILUMENAL FLEXIBLE MEDICAL DEVICE

RELATED APPLICATIONS

This application is a Continuation-in-Part of U.S. Patent Application Ser. No. 12/660,058, filed Feb. 19, 2010, now abandoned, which is Continuation-in-part of U.S. patent application Ser. No. 11/784,142, filed Apr. 5, 2007, now U.S. Pat. No. 7,704,234.

INTRODUCTION

The present teachings relate to devices and methods for producing a variably flexible stylet or other component utilized in a bi-lumenal flexible medical device.

BACKGROUND ART

Numerous devices have been developed to address the recurring issue of maximizing the mechanical properties of a catheter or other medical access device to be advanced through a lumen. One such key property is generally referred to in the art as "pushability," a term used to describe the rigidity of a device and its ability to advance through a lumen. See as an example U.S. Pat. No. 7,022,106. Another such property is the flexibility of a device. It is desirable for a device to be flexible enough to allow the device to traverse contorted and curved scopes and passages in the body. At the same time, the tip rigidity allows the device to better penetrate tissue, and the "pushability" allows proximal force transmission to the distal tip. Most composite materials provide for the flexibility needs, but do not meet the tip rigidity and pushability needs. Stainless steel provides very good rigidity and pushability, but is very limited in terms of flexibility.

Accordingly, companies have utilized various machining techniques in an attempt to impact these key properties. Current patents and technology have employed relief notches in both stylets and cannula tubing in an effort to increase flexibility. One example of such "static" flexibility is described in U.S. Patent Application Publication No. 2004/133124 to Bates, et al. Bates discloses a cannula and a stylet with notches designed to increase flexibility, but only in one plane of operation. However such notching does not allow for custom or adjustable flexibility and rigidity that is required in many medical procedures. As a result, such a device is flexible only in a fixed, constant or a "static" manner, and is thus of limited usefulness.

As one example of desired dynamic flexibility, it is necessary in certain procedures that the distal tip section initially be more flexible in order to accommodate tip deflection of a scope or introducer. As the device tip protrudes from the scope/introducer, it becomes more rigid, while at the same time the subsequent distal section is made more flexible to accommodate passage through the deflected scope/introducer. Under current art and designs, there is no method or device that will allow for this real-time modification and/or adaptation of flexibility. Such "tunable flexibility" features that are variable, adjustable and dynamic have broad application for endoscopic, bronchoscopic and laparoscopic procedures. Such technology could also be applied to intravascular, neurosurgery, optical procedures and a broad range of minimally invasive surgical procedures.

For instance, certain procedures require the device to navigate acute 135° angles during certain intralumenal operations. ERCP (endoscopic retrograde cholangiopancreatography) procedures require such convoluted paths and are becoming much more popular due to the improved patient outcomes derived through this technique. The procedure requires considerable flexibility, and considerable device length. However, with standard flexible materials, the longer the device is, the less "pushability" it will have at the tip of the device. Specifically, current technology makes use of conventional devices very difficult or impossible for ERCP. Current technologies are either too rigid to approach the desired target areas, or too flexible to effect any force transmission to the distal tip if they do achieve the target site. There are no known technologies that allow a material to be "tunable" with both good flexibility and good pushability within the desired portions of the same device, or flexible in the desired place of flexibility.

Current patented technologies describe only very simplistic relief notches that are in no way customized or engineered to allow variability in material performance, and provide only static flexibility. For instance, the medical device described in U.S. Pat. No. 6,419,641 may be too flaccid upon exiting the curved introducer to penetrate and obtain an adequate tissue core specimen in a "hardened" sclerotic liver. Conversely, the distal tip of said device may be too rigid to traverse a tighter than normal curve in the introducer as is required from time to time. In addition, the '641 patent is completely "static" in its operation, in that the flexibility designed into the device occurs only at one location, and in one plane. Thus, it actually teaches away from the dynamic flexibility enabled by the present teachings. Similarly, the device disclosed in U.S. Patent Application Publication No. 2004/133124 to Bates, et al. teaches away from the concept of "tunable" flexibility. The device described in Bates defines notches in the cannula and stylet that "face in the same direction" to allow flexibility in only one plane, namely "the plane perpendicular to the plane of the notch." Thus, again, flexibility is not turnable, it is found only at a given device location and is solely in one place. The Roth device design manufactured by Cook exhibits some flexibility, but does not transfer cutting energy to the distal tip effectively enough to obtain adequate biopsy samples. Conventional fine needle aspiration devices also suffer from a similar lack of effectiveness in transferring force for penetrating the surface of the target area. Forceps designed for tissue removal and retrieval are also unable to penetrate beneath the surface of the target site in many instances.

Accordingly, there is a need among physicians for devices that can traverse contorted and curved introducers and endoscopes while maintaining the option of a maximum amount of tip rigidity and pushability in the distal and other segments of the device, as needed, and that is adaptable to numerous procedures, such as biopsies of the pancreas, bile duct, or of "hardened" or sclerotic liver. There is a further need for a technology that allows for such a device to exhibit custom tunability of flexibility at specific points along the length of the device.

One mechanism for manufacturing a stylet according to the teachings herein requires custom machining of certain notch sets into the length of the stylet at predetermined places. Although machined notches (including ground, laser, etc.) in stylets can achieve dynamic performance profiles, the machined notches can currently pose cost challenges for mass produced bi-lumenal devices. Accordingly, there is a need for suitable manufacturing methods to create inexpensive stylets that flex in separate fields as described herein.

SUMMARY

The Dynaflex technology of the present teachings advantageously utilizes both simplistic and sophisticated notch designs, as determined and custom-engineered for specific applications. Utilizing the technology and methods disclosed herein, the device characteristics of flexibility and rigidity can be adapted by the physician or device manufacturer according to the type of procedure, the patient size and unique anatomical challenges of a given procedure. Rigidity and flexibility can be actively controlled by an operator at predefined portions of the device through rotating the stylet within the cannula to bring about alignments of customized notches to impart target flexibility or rigidity profiles at specific spots on the device. This alters the relationship and orientation of specific notched and non-notched segments of either or both the stylet and cannula that are strategically located at said critical points along the length of the device.

BRIEF DESCRIPTION OF THE DRAWINGS

The skilled artisan will understand that the drawings described below are for illustration purposes only. The drawings are not intended to limit the scope of the present teachings in any way.

FIG. 1 is a prior art stylet (or wire) showing side and front views and planes of maximum flexibility and maximum rigidity.

FIG. 2 is a prior art cannula (or tubing) showing side and front views and planes of maximum flexibility and maximum rigidity positions.

DESCRIPTION OF VARIOUS EMBODIMENTS

Figure 3:
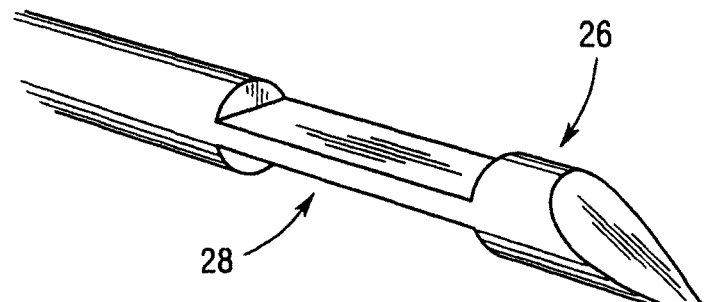
FIG. 3 depicts a double notched stylet according to an embodiment of the present teachings.

The present Dynaflex technology enables intralumenal medical access devices to exhibit previously unheard of control over flexibility and pushability at pre-designated portions of the instrument. The technology allows a device operator to custom tailor the flexibility and rigidity of given sections of devices through rotational, axial alignment, and manipulation of the orientation of the stylet to the cannula and to each other.

As used herein, the term "cannula" refers to any outer component of a device such as a coaxial device, and includes an outer hollow needle, which is typically stainless steel, but is capable of being manufactured using other materials. The cannula has a cannula wall, ordinarily comprising a thickness of between about 0.003" and 0.200", a distal end, and a proximal end. The cannula wall is designed to accept an inner needle with a maximum outer circumference equal to or less than the minimum inner diameter of the cannula.

As used herein, the term "stylet" refers to any inner component of a coaxial device, and includes a "wire" or needle that is slideable within a corresponding cannula with a proximal end, a distal end, and a functional end or tip that is designed to perform or assist in a designated medical procedure. This can include, for example, cutting a small biopsy sample, and can also include a hollow needle or "inner cannula" for penetrating and retrieving a target sample. For such hollow needle uses, typical gauges for the majority of medical uses are about 18, 19 or 20. However the present technology can be utilized with any gauge.

As used herein, the term "intralumenal device" refers to any multiple coaxial devices, including but not limited to a notched stylet and cannula set, a tube within a tube, or other component devices that comprise two or more coaxial components that can be used in medical treatment or diagnosis.

As used herein, a "notch set" refers to a cannula notch set or a stylet notch set. The depth of the notch set can be partial, or it can penetrate the full dimensions of the device component. Where there is such penetration, it may be necessary to include inner cannula sheaths or coatings to seal the penetrations to ensure the ability of the device to aspirate under vacuum, or to otherwise extract the sample or specimen. Such coatings can be polymeric in nature, allowing flexibility and the necessary seal, as are well known to those skilled in the art.

As used herein, the term "cannula notch set" refers to a series of one or more notches or etchings and the corresponding unetched or un-notched areas, occurring approximately at a fixed point along the length of the cannula which can be of equal length and/or equidistantly axially spaced, or alternatively, can be of varying length and spacing.

As used herein, the term "stylet notch set" refers to a series of one or more notches and the corresponding unnotched areas, occurring at fixed points along the length of the stylet which can be of equal length and/or equidistantly axially spaced, but can also be of varying length and spacing.

Figure 4A:
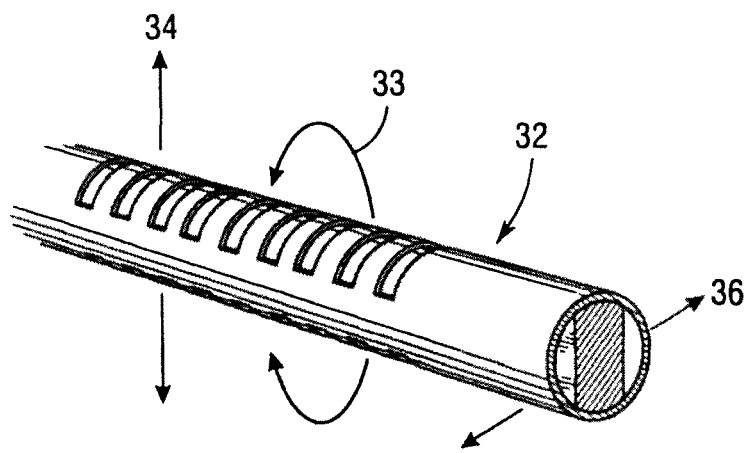
FIG. 4 depicts cross sections of the cannula in conjunction with the stylet of the present teachings inside oriented for both maximum flex and maximum rigidity positions.
Figure 4B:
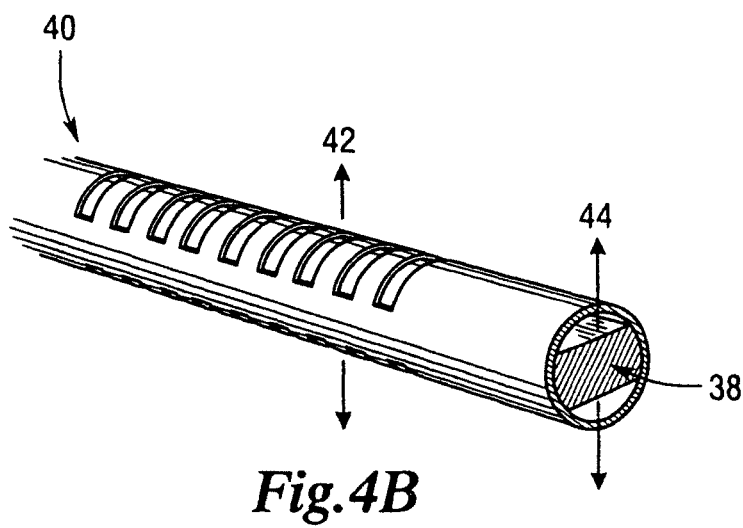

As used herein, "radial alignment" refers to a point at which the centerpoint of a cannula notch is aligned with either the centerpoint of a stylet notch or the centerpoint of its un-notched segment, as depicted in FIGS. 4A and 4B.

As used herein, "linear alignment" means a point along the functional linear length of the device wherein any stylet notch set and any cannula notch set are aligned.

The present teachings rely upon a novel dynamic orientation between the custom engineered stylet and cannula components in order to vary the flexibility and/or rigidity in given section(s) of the intralumenal device. As one example, the distal tip section of a device with notch sets, as depicted in FIG. 5, can be made more flexible by an operator where the stylet and cannula notch sets are in radial alignment, as depicted in FIGS. 4A and 4B. This design accommodates tip deflection of the scope or introducer. As the intralumenal device tip protrudes from the scope or introducer, the exact same segment of the device tip can be made more rigid by the operator by rotating the stylet 90° within the cannula, so that the initial segment becomes rigid, as depicted in FIG. 4A, and thereby causing this first section to transform from flexible to rigid, and a second section to transform from rigid to flexible, as depicted in FIG. 4B. In this fashion, the tip becomes rigid, while the subsequent distal section is made more flexible in order to accommodate passage through the deflected scope or introducer. This is one simple example of a flexibility profile for a device that utilizes the design, engineering methods, and materials of the present teachings. These features have particular application for endoscopic, bronchoscopic and laparoscopic biopsies, for example.

An operator of an intralumenal device utilizing the present technology can make a section of the device alternatively rigid or flexible in real time as it transverses the introducer or scope. The lead section can be more flexible to transverse the deflected scope tip while the following section is more rigid to allow pushing and/or force transmission from the proximal end. By the operator simply rotating the stylet of the present device 90° within the cannula, the reverse occurs: the lead section becomes more rigid as it protrudes from the scope, and the following section becomes more flexible to accommodate the deflection of the scope.

Multiple relief notches or etchings, comprising "notch sets" are positioned perpendicular to the longitudinal axis of the device. In some embodiments, these notches within a notch set of a cannula initiate at 0° and 180° and involve an arc of less than 180°. In some embodiments, the radial arc of the notches is between about 30° and 120°, thereby resulting in perpendicular sections within a notch set of about 150° and 60° remaining solid and "unnotched." The stylet relief notch set(s) in the distal section is oriented at the 180° position for greatest flexibility, wherein the notch set(s) at that area are in radial alignment. The stylet is then rotated 90° by the operator to realize maximum rigidity for the distal section, wherein the notch sets are perpendicular to this radial alignment. The next section of the stylet has a relief notch perpendicular to the lead distal section. This allows the second section to be out of phase with the first section and the cannula etchings.

Figure 8A:
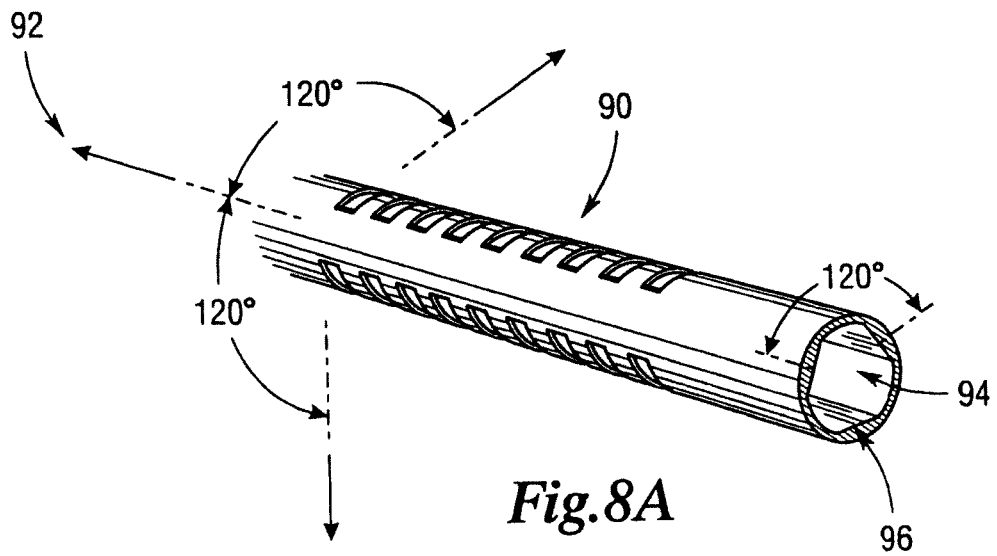
FIG. 8 depicts alternative notch sets at 120° radially, and 330° radially, respectively.
Figure 8B:
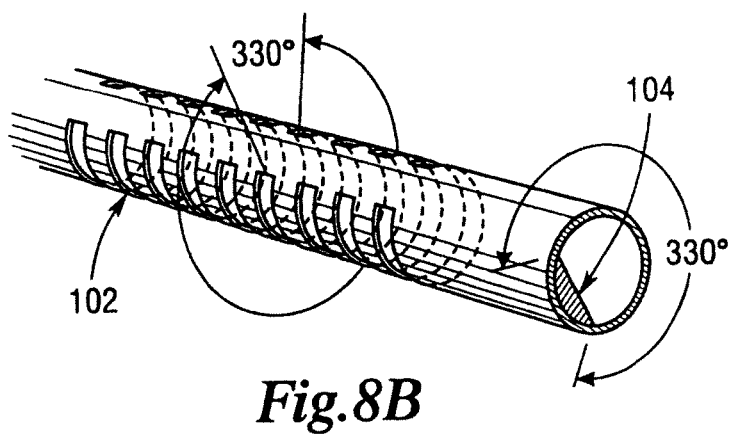

Utilizing methods of the present teachings, the device designer or operator can "map" the flexibility profile(s) required for a given procedure. By "mapping" alternating sections of the length of a device component with notch set(s) of varying axial orientation, and varying degrees of flexibility and pushability, the instrument can be designed to exhibit customized and controlled characteristics at and along unique portions of the instrument. The amount of flexibility and pushability can be carefully engineered and controlled at the time of design for a particular intralumenal device. By controlling the arc length of the notch sets, the frequency and the location of notch sets, transitions, the degree of phase change, and the notch dimensions, a broad range of flexibility can be "tuned" into the device by its operator, during a procedure. The shorter the arc of the notch, the less flexibility the device will exhibit at that point of radial alignment. However, as depicted in FIG. 8B, the arc can be up to 330°, which advantageously imparts significant flexibility to that particular device segment.

Various techniques can be used in order to create the slots or notches necessary to impart the desired flexibility to the device of the present invention. In some embodiments, a laser assisted micromachining technology developed by Creganna Medical Devices, Ireland (the "Creganna technology") is employed. In the Creganna technology, the cannula has custom designed slotting, both as to the axial arc radius of the slots, the longitudinal spacing of the slots, and the width of the slot itself.

A device according to an embodiment of the present teachings, and manufactured in part by Creganna Medical Devices to the following specifications, is described below for purposes of illustration.
    Inner diameter of cannula of about 0.90 mm
    Stylet outer diameter of about 0.866 mm
    160 mm laser cutting radius about 10 mm
The preceding cannula and stylet set can be used for:
    Tissue removal and sampling
    Device implantation (e.g. stents, radioactive seeds)
    Foreign object removal
    Therapeutic procedures (e.g. angioplasty, sutures)

Further benefits of the present device include the ability to dynamically control the flexibility and rigidity characteristics of given segments through convoluted difficult passages and transmission of necessary mechanical energy from the proximal device to the distal tip without compromising flexibility at the points along the length of the device.

Maximum flexibility of the device or a portion of the length of the device is achieved when the center point of a cannula notch set is aligned with the center point of the corresponding stylet notch set. Alternatively, maximum rigidity of the device is achieved when the center point of a cannula notch set is in line with the center point of the non-notched, rigid sections corresponding to the stylet notched set. This relationship holds true regarding both flexibility and rigidity, regardless of the number of slotted regions and the length of the slots. As indicated in FIG. 8A, it is not essential for the notch sets to be oriented at 180°. The notch sets can be oriented at 120°, or other unique geometries that will be apparent to one skilled in the art.

Moreover, various gradations of flexibility and device characteristics can be achieved as the device is "tuned" by rotating the stylet from the point of radial alignment through to the point where the centerpoint of a stylet notch is furthest away from the centerpoint of the notch(es) contained in the stylet.

The present teachings also allow for an unexpected operating characteristic. This characteristic involves the inherent "steerability" of the intralumenal device. Because the device has dynamic flexibility with axial rotation, when the catheter tip encounters resistance, the resistance translates to torque on the length of the device, and this torque causes the stylet to rotate axially within the cannula at the point of resistance, thereby causing an increase and an automatic adjustment of flexibility where the rotation brings notch sets closer to radial alignment. Thus, this intralumenal resistance automatically brings about a change in flexibility at that point. These dynamic and varying characteristics can be used by the operator to navigate and to even "steer" the device as it progresses through an intralumenal procedure. For many medical devices applications, two regions with notches, as depicted in FIG. 5, are desirable. However, other configurations are possible. For instance, where notch sets consist of three notches, instead of two, device flexibility is directly impacted in three directions, maximally at 120° radially. As depicted in FIG. 8A, notches oriented at 120° allow a device to be maximally flexible in three different planes, and with a different flexibility profile than if the notches were oriented at 180°.

Importantly, the notch set can also comprise one notch. In some embodiments, this notch can be as great as 330°. In some embodiments, the range for a single slotted notch set is between about 180° and 300°. A single notch set of 330° is depicted in FIG. 8B.

Figure 10:
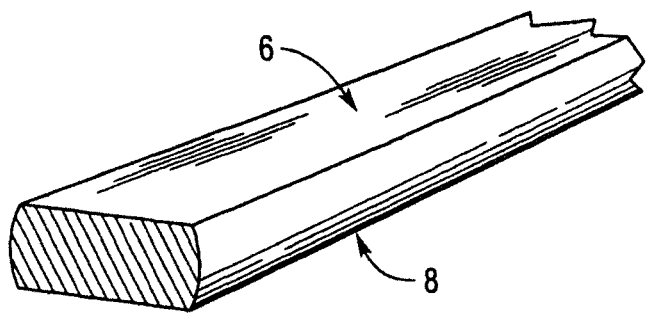
FIG. 10 depicts a stylet component with two machined planar surfaces in accordance with the present teachings.

Alternatives to the foregoing notch machining and manufacturing techniques may in some instances provide a preferable approach for certain medical devices, including where significant portions of the stylet are required to be flexible in one direction or another or in devices that are produced in large quantities. In such instances, the approach of laser machining and notching the stylet may prove technically challenging and/or expensive. In an alternative method of manufacturing the stylet devices of the present teachings, the stylet is machined or formed from rodstock to include two flat machined "sides", 6 and 8, along a portion of the length of the stylet, as depicted in FIG. 10. As used herein, the term "machined" means that the "sides", 6 and 8, may be created from a variety of methods including during the extrusion process for the stylet stock or may be rolled, drawn or ground from standard cylindrical stock snapes, or may be machined from a standard cylindrical stock shape. As used herein, the "stock" may be stainless steel, or polymers such as Nitynol, and other polymers with thermoset characteristics, and any other alloys or composites that may be machined and maintain necessary ductility.

Figure 11A:
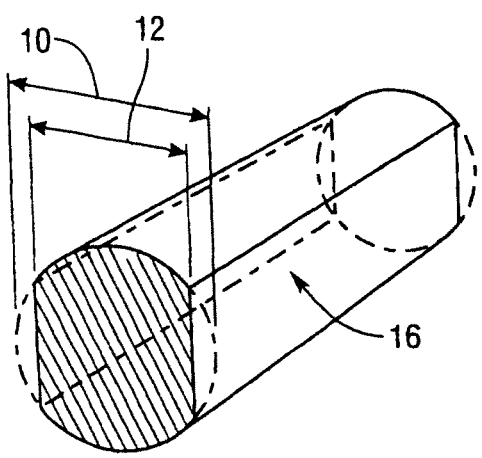
FIGS. 11A and 11B depict a sample range in cross sectional length of the planar surfaces relative to the diameter of the stylet stock.
Figure 11B:
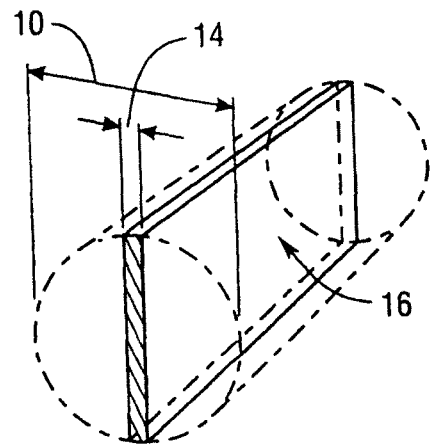
Figure 12:
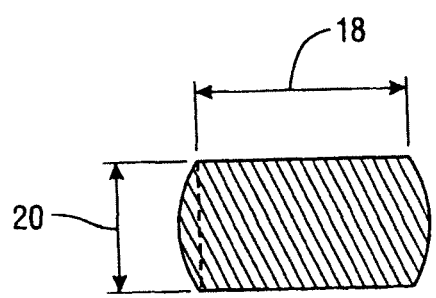
FIG. 12 depicts the relationship in length between the remaining chord of the diameter of the stylet stock, and the planar surface.

As depicted in FIG. 11, the process of machining the two flat sides may selectively reduce the dimension of the stock by 10% of the original diameter of the cross section, 10, to 90% of that diameter, 12, to over 90% of the original diameter of the cross-section, 14, with planar surfaces, 16, for the stylet stock. As depicted in FIG. 12, the cross sectional length of the planar surface, 18, is, in some embodiments, greater than the length of the remaining chord of the stylet stock diameter, 20. Thus, although the planar surface can be as small as depicted in FIG. 11A, greater flexibility is imparted into the stylet when the ratio between the diameter of the stylet stock and the length of the planar surface is comparable to that shown in FIG. 11B.

Figure 13:
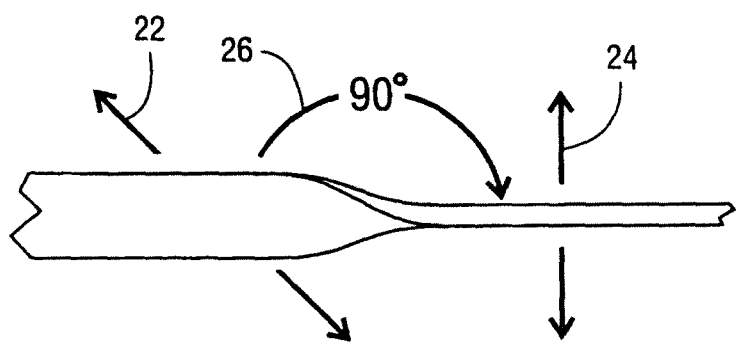
FIG. 13 depicts a bend in orientation of the single machined planar surface according to the present teachings.

After one or more sides of the stylet has been machined or formed along the desired length of the stylet, the resulting stylet is then subjected to precise radial bending at key locations along the stylet where the engineering of a dynamic change in flexibility of the device is desired. As depicted in FIG. 13, the planar surfaces of the stylet are oriented in one direction on one end of the bend, 22, and in another direction on the other side of the bend, 24. The angle of this change, 26, in alignment of the two planar surfaces, 22 and 24, located at the point of the bend, is 90°, 26, in some embodiments, but can comprise any angle of bend that imparts a desired plane of flexibility into the stylet and medical device at that particular point along the length of the stylet.

The resulting machined stylet operates in a similar fashion to the stylets depicted in FIG. 3. When the portion of the machined stylet that maintains the full diameter of the original stock is in parallel orientation to the notch sets in the cannula, the device exhibits maximum rigidity at that point. When the machined stylet is axially rotated so that the planar surfaces are in parallel orientation to the notch sets in the cannula, the device then dynamically transforms to exhibit maximum flexibility at said point.

Numerous bends in the planar orientation can be made to the stylet at the desired portion along the length of the stylet, thereby imparting customized flexibility profiles as described by the present teachings. An example of a stylet that has multiple bends and thus multiple planes of flexibility at those points is set forth in FIG. 14.

The degree of flexibility of the present device at the point of certain bends can be controlled in part by the amount of the round stylet that is machined in the initial step or the width of the cross sectional flat surface, 18. This percentage, which can range from about 10% to 90% in some embodiments and from about 30% to 60% in other embodiments, may itself vary along the length of the stylet, so that certain portions of the stylet exhibit increased flexibility over other portions.

In addition to the low cost of creating custom stylets based on the present teachings, the methods herein also impart into the stylet an unexpected mechanical property by altering the inherent metallurgical properties of the stylet stock. When the stock is bent through application of radial torsional forces such as at the numerous points, 28, designated in FIG. 14, the parallel orientation of stresses introduced when the stylet stock was originally drawn are altered. Because there is no stress riser at that point, there is less risk of sheering, and greater inherent integrity of the material. This results in greater cross sectional stability at the point of the bend, translating into enhanced "pushability" of the device, as that term is described herein.

Yet another method for manufacturing stylets with varying degrees of flexibility involves machining a groove into a rodstock suitable for a stylet. The groove can be machined along all or a portion of the length of the stock for the stylet. In order then to impart varying degrees of flexibility, standard polymer materials are used to fill the notch along portions of the length of the stylet thereby imparting less flexibility, depending upon the extent of polymer fill. The polymer can be selectively used to fill the notch along the stylet. The amount of polymer can be varied in order to "tune" or customize the amount of flexibility, and the nature of the polymer can be altered to impart various gradients of resulting flexibility. For instance, certain polymers such as thermoplastic elastomers, including polyether block amides, and including for instance polyurethane and polyethylene Pebax, exhibit rigidity and stiffness greater than that of other polymers and can be used to fill the stylet in this method.

In addition to the foregoing techniques, and in accordance with the teachings of the invention herein, several grooves can be machined along the length of the stylet stock at various locations along the circumference of the stock in order to provide flexibility in different planes along the stylet.

Yet a further method for manufacturing a flexible stylet involves the incorporation of three of more "flatwire" segments into the construction of a stylet at such locations where the operator requires flexibility. Because the three or more separate flatwire sections normally require additional length when bent convexly, and require a pocket for compression when bent, there is a need to assemble the three flatwires in such a configuration as to allow for accommodating these dimensional requirements when the stylet is flexed. This can be accomplished by constructing the stylet such that distal ends of both outside flatwire are attached at opposite ends of the stylet but are "free floating" at their opposing ends, with integral space to accommodate the full length of each flatwire when the stylet is bent in a concave position.

FIG. 1 depicts a prior art stylet, 10. The stylet contains a cut out notch, 12, which allows the stylet flexibility in one plane, 14, that is perpendicular to the radius of the notch cut marked A and allows the stylet greater flexibility in that plane, but retains rigidity in field of motion of the opposite plane, 16, motion.

FIG. 2 depicts a prior art cannula, B. The cannula contains notch sets, 20, machined into its surface that allow the cannula greater flexibility in one plane, 22, marked A that is parallel with the centerpoints of the matched areas of the notch set, 24, but retains rigidity in the perpendicular field of motion marked "B." When the stylet, 10, is used in conjunction with the cannula, 18, there is maximum flexibility only in one plane of motion.

FIG. 3 depicts a double notched stylet, representing an embodiment of the present teachings. The stylet, 26, comprises two machined notches, 28, imparting flexibility into the stylet in one direction, at the point of the notches. It is not necessary to practice the invention for the stylet to contain double notches. Similarly, it is not necessary for the cannula depicted in FIG. 4 to have mirror image notches. In fact, in many instances, a single notch can suffice. The depth of the notch can be more than 50% of the cross section of the stylet, and can be up to 90% or more, so long as there remains sufficient material to provide pushability and integrity of the stylet at the point of the notch.

FIG. 4 depicts the dynamic flexibility range of the device of the present teachings. FIG. 4A depicts a cross section of a cannula/stylet set, wherein the cannula, 32, contains two notched sections, 33, on opposite sides of the cannula. In FIG. 4A, the plane of flexibility of the cannula, 34, is perpendicular to the plane of flexibility of the stylet, 36. This results in an orientation of stylet and cannula that is minimally flexible. However, as depicted in FIG. 4B, where the stylet, 38, is rotated within the cannula, 40, 90° so that the planes of flexibility, 42 and 44, are parallel, and thus in radial alignment, the same stylet and cannula can exhibit a profile of maximum flexibility. It is not necessary that the cannula contain two sets of diametrically opposed notches; if the notch is sufficiently large in radius, one notch can impart a sufficient degree of flexibility when the stylet is in axial alignment.

Figure 5A:
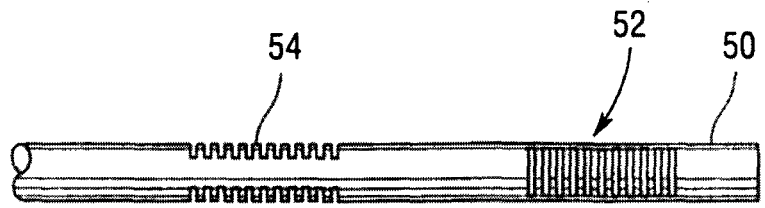
FIG. 5 depicts custom notch sets according to the present teachings that simultaneously allow tuned flexibility in different planes.
Figure 5B:
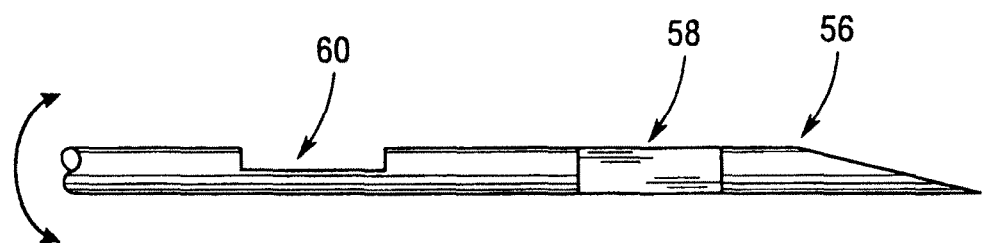
Figure 5C:
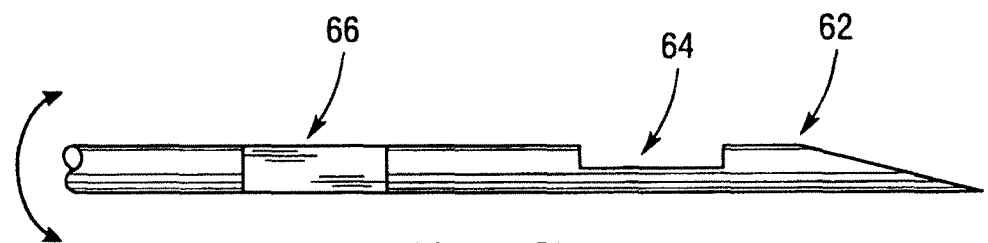

FIG. 5 depicts a cannula and notch set that allows a single set to demonstrate customized flexibility in different planes, at different points along the length of the cannula. The cannula of FIG. 5A, 50, contains two notch sets, 52 and 54, that allow flexibility in planes perpendicular to each other. The stylet, 56, in FIG. 5B depicts two notches, 58 and 60, that, when inserted into the cannula in the orientation depicted in FIG. 5A, results in maximum flexibility at both points of flexibility. However, the stylet depicted in FIG. 5C, 62, when inserted into the cannula oriented as depicted in FIG. 5A, would result in a profile of maximum rigidity at the points of both notches, 64 and 66. Importantly, the cannula/stylet set flexes in one plane of direction at one notch set, 52, and simultaneously in another direction at the second notch set, 54, when the corresponding notch sets are in lineal alignment. As the stylet is advanced, the stylet's first initial notch 58 and 64, first encounters the cannula notch, 54, and depending upon its radial orientation, is either flexible or rigid at that position.

Figure 6:
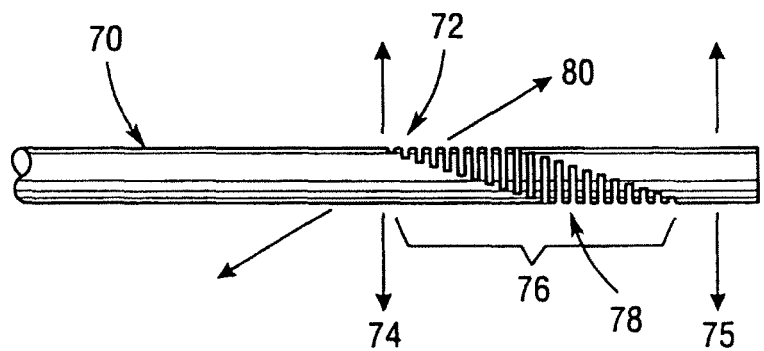
FIG. 6 depicts a dynamically flexible transition profile of a cannula in accordance with the present teachings.

FIG. 6 depicts a further customization of flexibility. When utilizing the methods of device design disclosed herein, a cannula, 70, can contain notch sets that progressively shift along the length of the cannula from one plane of flexibility, as at notch set, 72, which allows flexibility in one plane, 74, through the length of the catheter, 76, and transitioning at a point along that length, 75, to a plane of flexibility, 80, perpendicular to the initial plane, 74. As the stylet depicted in FIG. 4A is passed through the cannula depicted in FIG. 6A at the same radial orientation, the flexibility profile in a given plane will progressively change as the operator advances the stylet through the cannula, achieving different points of linear alignment.

Figure 7:
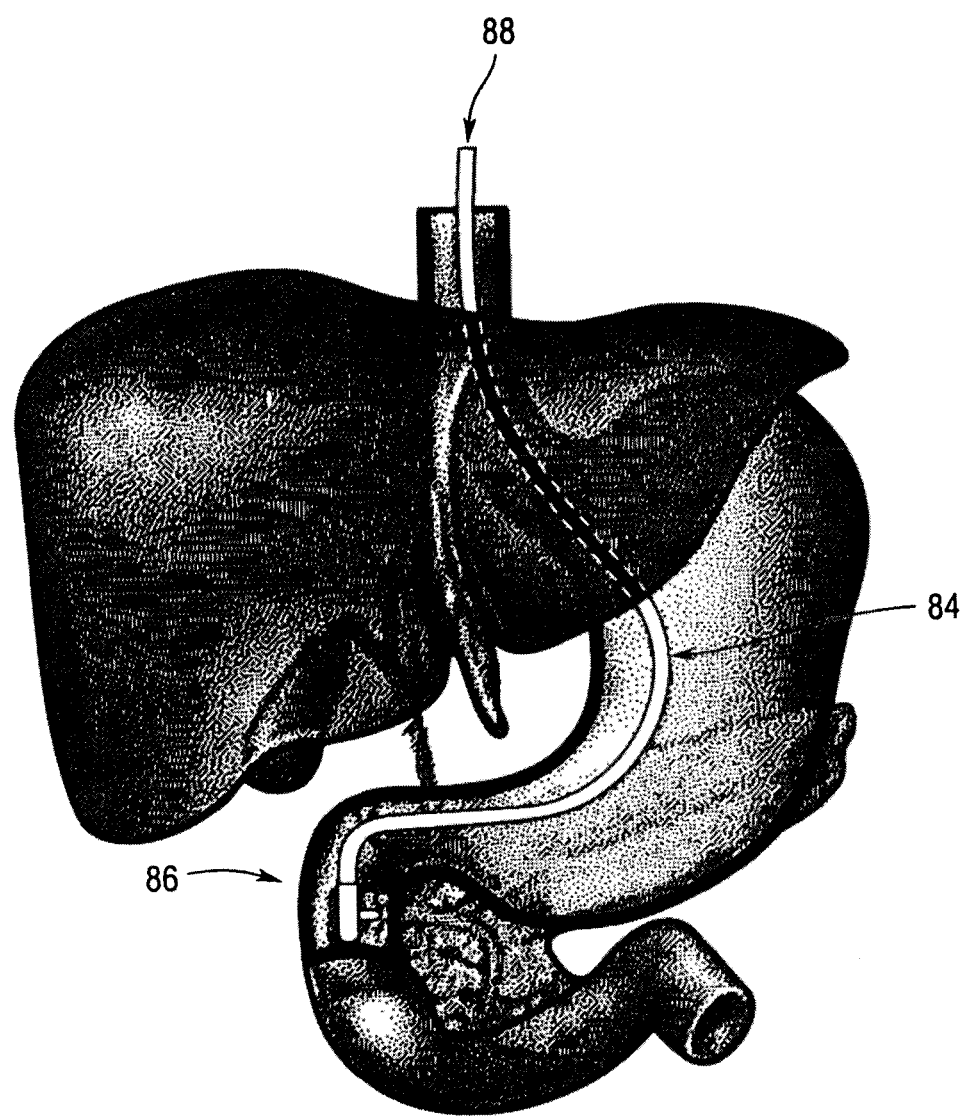
FIG. 7 depicts the human anatomical required path of an intralumenal medical device to perform an ERCP.

FIG. 7 depicts a cross sectional anatomical view of the path of an intralumenal device necessary to perform an ERCP procedure. As depicted, the device, 84, is required to navigate significant bends and turns as it advances through the patient. At some locations, the device must conform to a 135° bend, 86. In addition, the device must be rigid, with good pushability, at the point of introduction, 88.

FIG. 8 depicts two examples of what may be an infinite number of custom engineered alternative notch sets that impart their own unique and custom flexibility and pushability profiles at those specific points of radial and/or lineal alignment along the length of an intralumenal device. FIG. 8A shows a notch set with three sets of cannula notches, 90 for which the center points are 120° apart. This allows for maximum flexibility in three separate planes, 92, as a stylet, 94 with three machined notches, 96, is axially rotated. FIG. 8B depicts a single notch set, with one cannula notch, 102, and one stylet notch, 104. When aligned at a point of radial alignment, the device exhibits maximum flexibility at that point of the device and at varying degrees of flexibility at other points of alignment, such as the point depicted in FIG. 8B.

Figure 9:
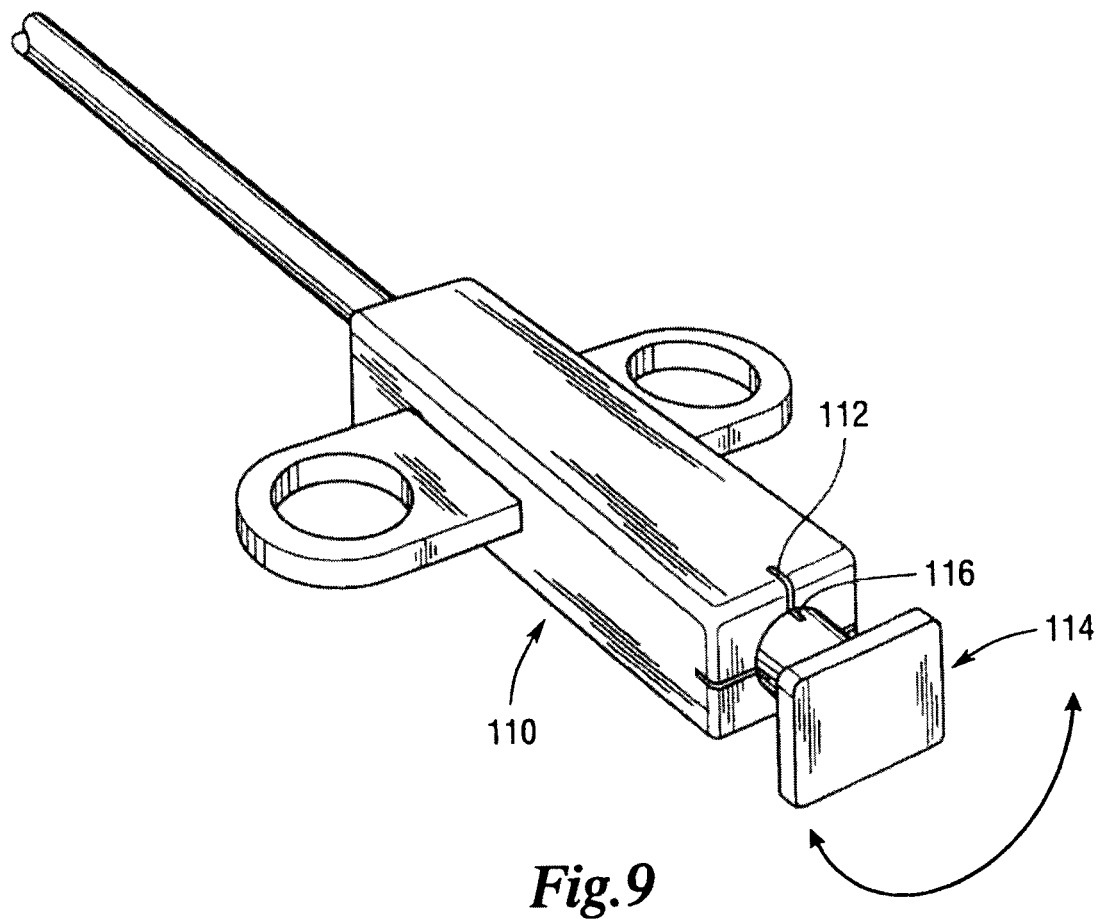
FIG. 9 depicts an operator's handle with rotation demarcations according to the present teachings.

FIG. 9 depicts an embodiment of the present teachings wherein the operator's handle, 110, contains reference demarcations, 112, as a reference to measure against similar demarcations on the stylet control, 114. As the stylet is axially rotated in either direction by the operator, as indicated, the demarcations on the stylet control, 116, can be referenced against the base handle, 110, to determine the orientation of the stylet to the cannula. Thus, at any predetermined point along the length of the device, flexibility can be specifically tuned into the device.

FIG. 10 depicts a cross section of a machined stylet manufactured pursuant to the present teachings.

FIGS. 11A and 11B depict the dimensional sizes of the machined surfaces relative to the original dimensions of the stylet stock.

FIG. 12 depicts the relative proportions of the machined flat surface and the length of the segment of chord remaining after machining.

FIG. 13 depicts the orientation of the planar surfaces after radial bending.

Figure 14:
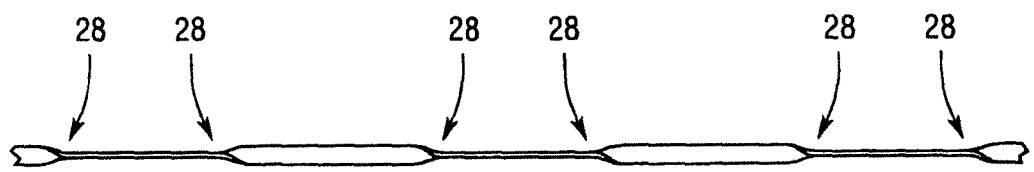
FIG. 14 depicts a device component of the present teachings which includes multiple bends in the stylet planar surface.

FIG. 14 depicts an example of a length of stylet manufactured according to the present teachings.

The number and length of the sections with cannula or stylet notch sets can be adjusted to accommodate specific applications. This concept can also be used for applications such as vascular access, guide wires, GI and pulmonary procedures.

Between any of said customized sections of a device, there can also be a transitional alignment to accommodate the advancement of the device from one section to another. One embodiment of such approach utilizes circumferential grooves in the transitional area to allow deflection in multiple planes but which are still adequate to transfer necessary force to the distal tip. An example of such a transition configuration is depicted in FIG. 6.

Also disclosed herein is a method for the design and fabrication of a tunably flexible intralumenal medical device. The method comprises the steps of identifying a medical procedure that involves the introduction of an intralumenal device into an intralumenal passage. The approximate internal route within the body is then determined, including the nature and extent of bends the device will be required to navigate in order to reach the point of care or treatment. This can, in certain circumstances, involve at least two or three important bends. The bends can involve simultaneous different planes of flex at different sections of the device. Utilizing the technology described herein, a device specific to that procedure which includes customized flexibility and/or pushability can be "created" by the device operator during the procedure at predetermined points along the medical device that correspond to the median placement of bends or device geometries presented by the anatomy of a statistically average subject (e.g., patient) undergoing the procedure in question. An example of such a customized medical device would be one designed to perform an ERCP biopsy, as depicted in FIG. 4.

Mathematical models are then utilized to optimize or "map" the geometry of each of the components as well as the overall device for specific applications where there is such a need for adaptation of rigidity and/or flexibility. This method allows for the successful development of optimal custom designs for numerous medical devices where such needs are vital.

The flexibility and pushability "mapping" for a specific procedure typically requires an operator to establish pre-set axial stylet and cannula orientations at specific points along the length of the intralumenal device. Such length markers would be clearly visible to the operator. The axial orientation can be defined, for example, on the introducer portion of the device, or on the handle, as depicted in FIG. 9. In various embodiments, the axial orientation can be correlated with corresponding demarcations along the length of the intralumenal device. Other methods of demarcating positions along the length of the device to alter the radial alignment of the device components, including the use of electronic means, are well known to those skilled in the art. These can include optical markers, or the utilization of embedded piezoceramics to signal a particular radial alignment at a point of linear alignment.

Although the present technology is uniquely suited for the design and manufacture of custom intralumenal medical devices, the technology and methods disclosed herein can also be suitably employed to design devices for industrial and other applications. For instance, custom flexibility may be required in an underground petroleum or gas well setting. Maintenance devices for pipes in nuclear facilities often require custom flexibility. Through utilization of a two piece mechanism with notch sets as described herein, such industrial devices can be designed to navigate very acute angles within pipes and fixtures, without compromising the pushability or effectiveness of the working end of the device.

The section headings used herein are for organizational purposes only and are not to be construed as limiting the subject matter described in any way.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

What is claimed is:

1. An intralumenal medical access assembly having longitudinal flexibility in at least two planes, comprising:
   a cannula having a longitudinal axis;
   a stylet longitudinally slideable within the cannula, the stylet being rotatable within and relative to the cannula about the longitudinal axis, the stylet including
   a distal end portion configured to cut tissue, and
   a flatwire portion proximal of the distal end portion, the flatwire portion having two planar surfaces facing away from one another, the flatwire portion having a twisted region along a length of the flatwire portion, the flatwire portion being rotationally twisted about the longitudinal axis at the twisted region, the twisted region dividing the flatwire portion into a first flatwire segment and a second flatwire segment,
   wherein the two planar surfaces at the first flatwire segment are rotationally offset from the two planar surfaces at the second flatwire segment.

2. The assembly of claim 1, wherein the first flatwire segment is rotationally offset from the second flatwire segment by about 90°.

3. The assembly of claim 1, wherein the first flatwire segment is rotationally offset from the second flatwire segment by an angle greater than 90°.

4. The assembly of claim 1, wherein the first flatwire segment is rotationally offset from the second flatwire segment by an angle less than 90°.

5. The assembly of claim 1, wherein the flatwire portion has a second twisted region along the length of the flatwire portion, the flatwire portion being rotationally twisted about the longitudinal axis at the second twisted region, the second twisted region defining a third flatwire segment of the flatwire portion,
   wherein the two planar surfaces at the third flatwire segment are rotationally offset from the two planar surfaces at at least one of the first flatwire segment and the second flatwire segment.

6. The assembly of claim 1, wherein the stylet has a length greater than about 20 mm.

7. The assembly of claim 1, wherein the cannula further includes a polymer sheath or a coating on its interior surface.

8. The assembly of claim 1, wherein the cannula includes a cannula notch set along its length.

9. The assembly of claim 8, wherein the first flatwire segment and the second flatwire segment are radially rotatable relative to the cannula to a degree of radial alignment with the cannula notch set, the degree of radial alignment causing a variable flexibility of the assembly at the radial alignment.

10. The assembly of claim 8, wherein the cannula notch set has a total arc length of about 30° to 330° of a circumference of the cannula.

11. An intralumenal medical access assembly featuring dynamic variable degrees of flexibility controlled in real time during a medical procedure, comprising:
   (a) a cannula with at least one cannula notch set along its length; and
   (b) a stylet having a length greater than about 50 mm, the stylet having two substantially parallel planar surfaces along a desired length of the stylet,
   wherein said stylet is both longitudinally slideable within and radially rotatable within and relative to said cannula at any position along a functional linear length of the cannula; and
   wherein at one or more points of longitudinal alignment along said cannula functional linear length, the planar surfaces are radially rotatable relative to the cannula to a degree of radial alignment with said at least one cannula notch set, said radial alignment causing a variable flexibility of the assembly at the point of alignment.

12. The assembly of claim 11 wherein the cannula notch set has a total arc length in the range of about 30° to 330° of the circumference thereof.

13. The assembly of claim 11, wherein the notch sets are machined through laser machining techniques.

14. The assembly of claim 11, wherein the cannula further includes a polymer sheath or coating on its interior surface.

15. An intralumenal medical access assembly having longitudinal flexibility in two or more planes, comprising:
   (a) a cannula with at least two cannula notch sets along its length; and
   (b) a stylet having a length greater than about 50 mm, the stylet having two substantially parallel planar surfaces along a desired length of the stylet,
   wherein said stylet is both longitudinally slideable within and radially rotatable within said cannula at any positions along a functional linear length of the cannula, and
   wherein said planar surfaces are flexible in a first plane at a point of radial alignment with a first cannula notch set and, upon radially rotating and advancing the stylet, are flexible in a second different plane at a second point of linear alignment and radial alignment at a second cannula notch set.

16. The intralumenal medical access assembly of claim 15, wherein a region of the assembly is rigid where a circumferentially central point of at least one cannula notch set is aligned with a central point of the stylet between the planar surfaces.

* * * * *